(12) United States Patent
Yasuda

(10) Patent No.: US 8,747,827 B2
(45) Date of Patent: Jun. 10, 2014

(54) EMULSIFIED COSMETIC COMPOSITION

(75) Inventor: Chihiro Yasuda, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 88 days.

(21) Appl. No.: 13/510,237

(22) PCT Filed: Dec. 10, 2010

(86) PCT No.: PCT/JP2010/072228
§ 371 (c)(1),
(2), (4) Date: Jun. 22, 2012

(87) PCT Pub. No.: WO2011/074489
PCT Pub. Date: Jun. 23, 2011

(65) Prior Publication Data
US 2012/0251481 A1 Oct. 4, 2012

(30) Foreign Application Priority Data
Dec. 15, 2009 (JP) ................................. 2009-283684

(51) Int. Cl.
*A61K 31/74* (2006.01)
*A61K 8/00* (2006.01)

(52) U.S. Cl.
USPC ........................................ 424/78.02; 424/401

(58) Field of Classification Search
USPC ............................................. 424/401, 78.02
See application file for complete search history.

(56) References Cited

U.S. PATENT DOCUMENTS

| | | | | |
|---|---|---|---|---|
| 6,150,425 A | * | 11/2000 | Sekine et al. | 516/22 |
| 2006/0257436 A1 | * | 11/2006 | Kaminuma et al. | 424/401 |
| 2011/0002873 A1 | * | 1/2011 | Omura et al. | 424/78.03 |

FOREIGN PATENT DOCUMENTS

| | | |
|---|---|---|
| JP | 5-262617 | 10/1993 |
| JP | 10-87475 | 4/1998 |
| JP | 2000239139 | 9/2000 |
| JP | 2001302434 | 10/2001 |
| JP | 2002-316915 | 10/2002 |
| JP | 2004-203825 | 7/2004 |
| JP | 2006-298834 | 11/2006 |
| JP | 2006-298834 A | 11/2006 |
| JP | 2008-247756 | 10/2008 |
| JP | 2009-215266 | 9/2009 |
| JP | B-4637086 | 10/2011 |
| WO | WO 02/12388 | 2/2002 |
| WO | WO 2009/093534 | 7/2009 |
| WO | WO 2009/093534 A1 | 7/2009 |

OTHER PUBLICATIONS

Clariant brochure, "Your universally applicable Polymer", 2007.*
Miwa, T., "Structural Determination and Uses of Jojoba Oil", JAOCS, Feb. 1984, vol. 61, No. 2, p. 407-410.*
JPO Notice of Reasons for Rejection of Jan. 14, 2011.
JPO Notice of Reasons for Rejection of May 13, 2011.
JPO Decision for Grant of Sep. 16, 2011.
Submitted written arguments to JPO of Mar. 14, 2011.
Submitted written arguments to JPO of Jul. 8, 2011.
Granted claims in JP-B-4837086.
PCT/JP2010/072228 International Search Report mailed Jan. 18, 2011, 2 pages-Japanese, 2 pages-English.

* cited by examiner

*Primary Examiner* — Gina C Justice
(74) *Attorney, Agent, or Firm* — Andrew F. Young, Esq.; Lackenbach Siegel, LLP

(57) ABSTRACT

An object is to provide an emulsified cosmetic composition which can impart satisfactory taut feeling and yet is free of stickiness, by incorporating polyvinyl alcohol into a soap-based emulsified cosmetic composition.
The present invention relates to an emulsified cosmetic composition comprising: (a) polyvinyl alcohol: 0.01% to 1% by mass; (b) a polyethylene glycol having a molecular weight of 15,000 to 25,000: 0.01% to 5% by mass; (c) a higher fatty acid; and (d) a neutralizing agent.

6 Claims, No Drawings

EMULSIFIED COSMETIC COMPOSITION

CROSS REFERENCE TO RELATED APPLICATIONS

This application relates to and claims priority from PCT/JP2010/072228 filed Dec. 10, 2010, the entire contents of which are incorporated herein by reference, and which in turn claims priority from JP 2009-283684 filed Dec. 15, 2009.

TECHNICAL FIELD

The present invention relates to an emulsified cosmetic composition, and more particularly, to an emulsified cosmetic composition which imparts taut feeling to the skin, moisturizes the skin while simultaneously imparting softness, and yet is free of stickiness.

BACKGROUND OF THE INVENTION

Higher fatty acid salts (soaps) generally have a satisfactory feeling of application on the skin and have excellent oil emulsifying properties, and therefore, higher fatty acid salts have been widely used as emulsifiers for cosmetic compositions and medicines. For example, cosmetic emulsions using soaps or combinations of soaps and nonionic surfactants as emulsifiers, are 0/W type emulsions containing approximately 3% to 30% by mass of oil, and are known to give a moist feeling to the skin.

Meanwhile, in cosmetic emulsions and the like, polyvinyl alcohol (PVA) has been incorporated in order to impart taut feeling to the skin after application. For example, Patent Document 1 discloses a composition in which predetermined amounts of a film-forming agent and an extract of fermented soybeans (natto) extract are incorporated, as an external preparation for skin which is comfortable to the skin, is free of stickiness, and gives satisfactory taut feeling to the skin. In this composition, polyvinyl alcohol is used as the film-forming agent.

Patent Document 2 discloses a composition containing predetermined amounts of a lower alcohol, spherical powders, a film-forming agent and an algefacient, as a skin cosmetic composition which has an excellent sense of tightening and excellent feeling of taut and yet is free of stickiness, and in which the state persists. In this composition, polyvinyl alcohol is used as the film-forming agent.

Patent Document 3 discloses a composition in which a carboxyvinyl polymer, polyvinyl alcohol or a derivative thereof, and 2-amino-2-methyl-1-propanol are incorporated, as an external preparation for skin having, in particular, excellent skin tightening effects such as a sensation of coolness and tautness, and having satisfactory formulation stability.

As such, taut (or resilient) feeling can be imparted to the skin by incorporating polyvinyl alcohol into those compositions that are applied on the skin, such as cosmetic products. However, there has been a problem that when polyvinyl alcohol is incorporated into, soap-based emulsions such as described above, the skin after application has increased stickiness.

PATENT DOCUMENT

Patent Document 1: JP-A No. 2000-34218
Patent Document 2: JP-A No. 2000-239139
Patent Document 3: JP-A No. 2001-302434

ASPECTS AND SUMMARY OF INVENTION

Problem to be Solved by the Invention

Thus, an object of the present invention is to provide an emulsified cosmetic composition which can impart satisfactory tautness and yet is free of stickiness, by incorporating polyvinyl alcohol into a soap-based emulsified cosmetic composition.

Means for Solving the Problem

In order to address the object described above, the inventors of the present invention conducted a thorough investigation, and as a result, the inventors found that stickiness can be suppressed while taut feeling is maintained, by incorporating a polyethylene glycol having a molecular weight in a specific range into a soap-based emulsified cosmetic composition containing polyvinyl alcohol.

That is, the present invention provides an emulsified cosmetic composition containing (a) polyvinyl alcohol: 0.01% to 1% by mass, (b) a polyethylene glycol having a molecular weight of 15,000 to 25,000: 0.01% to 5% by mass, (c) a higher fatty acid, and (d) a neutralizing agent.

Effect of the Invention

The emulsified cosmetic composition of the present invention is a soap-based emulsified composition containing polyvinyl alcohol and a polyethylene glycol having a predetermined molecular weight, which is free of stickiness, gives satisfactory taut feeling to the skin after application, and also has an excellent effect of moisturizing and softening the skin.

BRIEF SUMMARY OF THE PRESENT INVENTION

Modes for Carrying Out the Invention

As described above, the emulsified cosmetic composition of the present invention contains, as essential components, (a) polyvinyl alcohol: 0.01% to 1% by mass, (b) a polyethylene glycol having a molecular weight of 15,000 to 25,000: 0.01% to 5% by mass, (c) a higher fatty acid, and (d) a neutralizing agent.

The polyvinyl alcohol (component a) used in the emulsified cosmetic composition of the present invention may be any polyvinyl alcohol that has been conventionally incorporated as a film-forming agent in cosmetic compositions and the like, and is not particularly limited; however, a polyvinyl alcohol having a degree of saponification of 80% or higher tends to be preferable in view of stability and effectiveness. The polyvinyl alcohol may be a product synthesized according to a conventional method, or may be a commercially available product. Examples of commercially available products include KURARAY POVAL (PVA-117H) manufactured by Kuraray Co., Ltd., and the like.

The amount of polyvinyl alcohol in the present invention is 0.01% to 1% by mass, preferably 0.01% to 0.5% by mass, and more preferably 0.01% to 0.1% by mass. If the amount of incorporation is less than 0.01% by mass, the taut feeling after application is not sufficient, and if the polyvinyl alcohol is incorporated in an amount exceeding 1% by mass, the cosmetic composition may have noticeable stickiness, and the stability of the preparation also tends to deteriorate.

The polyethylene glycol having a molecular weight of 15,000 to 25,000 (component b: hereinafter, referred to as "polyethylene glycol") used in the emulsified cosmetic composition of the present invention is a polymer of ethylene oxides, and as long as the average molecular weight of the polymer is in the range of 15,000 to 25,000, there are no particular limitations. Commercially available products can also be used, and examples thereof include PEG-20000 manufactured by Sanyo Chemical Industries, Ltd., and the like.

The amount of the polyethylene glycol in the present invention is 0.01% to 5% by mass, preferably 0.01% to 2% by mass, and more preferably 0.01% to 1% by mass. If the amount of incorporation is less than 0.01% by mass, the effect of suppressing stickiness is not sufficiently obtained, and if the polyethylene glycol is incorporated in an amount exceeding 5% by mass, stickiness is rather produced in some cases.

The cosmetic composition of the present invention is an emulsified cosmetic composition using a higher fatty acid (component c) as an emulsifier. There are no particular limitations on the higher fatty acid used in the present invention, as long as higher fatty acids that have been conventionally used as anionic emulsifiers in cosmetic compositions and the like, are used. Examples thereof include lauric acid, myristic acid, palmitic acid, stearic acid, isostearic acid, behenic acid, oleic acid, 12-hydroxystearic acid, undecylenic acid, tall acid, isostearic acid, linolic acid, linoleic acid, eicosapentaenoic acid (EPA), and docosahexaenoic acid (DHA). These higher fatty acids can be incorporated singly or in combination of two or more kinds.

Among the higher fatty acids, it is preferable to use one kind or two or more kinds of fatty acids having 14 to 22 carbon atoms, and for example, when three kinds of fatty acids, namely, isostearic acid, stearic acid and behenic acid, are used in combination, satisfactory characteristics are obtained.

The amount of incorporation of the higher fatty acid according to the present invention may be the amount that is conventionally employed in soap-based emulsified cosmetic compositions.

Examples of the neutralizing agent (counter-alkali) that forms a soap with the higher fatty acid include hydroxides of alkali metals, such as potassium hydroxide and sodium hydroxide; and basic nitrogen-containing compounds such as 2-amino-2-methyl-1-propanol, 2-amino-2-methyl-1,3-propanediol, triethanolamine, diethanolamine, monoethanolamine, triisopropanolamine, 2-amino-2-hydroxymethyl-1,3-propanediol, L-arginine, L-lysine, and N-alkyltaurine salts. These neutralizing can be used singly, or two or more kinds can be used in combination. The amount of incorporation of the neutralizing agent is appropriately determined in accordance with the equivalent of the higher fatty acid to be used.

Furthermore, the emulsified cosmetic composition of the present invention may also contain a nonionic surfactant in addition to the higher fatty acid (anionic surfactant).

The nonionic surfactant can be incorporated by appropriately selecting a lipophilic or hydrophilic nonionic surfactant in accordance with the formulation.

Examples of the lipophilic nonionic surfactant include sorbitan fatty acid esters such as sorbitan monooleate, sorbitan monoisostearate, sorbitan monolaurate, sorbitan monopalmitate, sorbitan monostearate, sorbitan sesquioleate, sorbtian trioleate, diglycerol sorbitan penta-2-ethylhexanoate, and diglycerol sorbitan tetra-2-ethylhexanoate; glycerin polyglycerin fatty acids such as mono-cottonseed oil fatty acid glycerin, monoerucic acid glycerol, sesquioleic acid glycerol, glyceryl monostearate, α,α'-glyceryl oleate pyroglutamate, and glyceryl monostearate malate; propylene glycol fatty acid esters such as propylene glycol monostearate; as well as hardened castor oil derivates, glyceryl alkyl ethers, and polyoxyethylene methylpolysiloxane copolymers.

Examples of the hydrophilic nonionic surfactant include POE sorbitan fatty acid esters such as POE sorbitan monooleate, POE-sorbitan monostearate, POE-sorbitan monooleate, and POE-sorbitan tetraoleate; POE sorbite fatty acid esters such as POE-sorbite monolaurate, POE-sorbite monooleate, POE-sorbite pentaoleate, and POE-sorbite monostearate; POE glyceryl fatty acid esters such as POE-glyceryl monostearate, POE-glyceryl monoisostearate, and POE-glyceryl triisostearate; POE fatty acid esters such as POE monooleate, POE distearate, POE monodioleate, and ethylene glycol distearate; POE alkyl ethers such as POE lauryl ether, POE oleyl ether, POE stearyl ether, POE behenyl ether, POE 2-octyldodecyl ether, and POE cholestanol ether; POE alkyl phenyl ethers such as POE octyl phenyl ether, POE nonyl phenyl ether, and POE dinonyl phenyl ether; pluaronic type compounds such as Pluronic; POE.POP alkyl ethers such as POE.POP cetyl ether, POE.POP 2-decyltetradecyl ether, POE.POP monobutyl ether, POE.POP hydrogenated lanolin, and POE.POP glycerin ether; tetra-POE-tetra-POP ethylenediamine condensates such as Tetronic; POE castor oil hardened castor oil derivatives such as POE castor oil, POE hardened castor oil, POE hardened castor oil monoisostearate, POE hardened castor oil triisostearate, POE hardened castor oil monopyroglutamate monoisostearate diester, and POE hardened castor oil maleate; POE beeswax.lanolin derivatives such as POE sorbite beeswax; alkanolamides such as coconut oil fatty acid diethanolamide, lauric acid monoethanolamide, and fatty acid isopropanolamide; as well as POE propylene glycol fatty acid esters, POE alkylamines, POE fatty acid amides, sucrose fatty acid esters, POE nonyl phenyl formaldehyde condensates, alkylethoxydimethylamine oxide, and trioleyl phosphoric acid.

The amount of incorporation of the nonionic surfactant is not particularly limited, and can be appropriately determined in a range suitable for stably emulsifying the system.

In the emulsified cosmetic composition of the present invention, other components that are conventionally used in emulsified cosmetic compositions can be incorporated to the extent that the effects of the present invention are not impaired. Examples of the components include vitamins, oils and fats, waxes, hydrocarbon oils, higher alcohols, synthetic ester oils, silicones, moisturizers, anionic surfactants, cationic surfactants, amphoteric surfactants, antiseptics, antiinflammatory agents, whitening agents, plant extracts, augmenting agents, blood circulation promoting agents, antiseborrheic agents, natural water-soluble polymers, semi-synthetic water-soluble polymers, synthetic water-soluble polymers, inorganic water-soluble polymers, thickeners, powder components, and sequestering agents.

The emulsified cosmetic composition of the present invention is mainly provided as a cosmetic composition for skin care, and can be provided in the form of a milky lotion, a cream, an essence, a sunscreen, or the like.

EXAMPLES

Hereinafter, the present invention will be described in more detail by way of specific embodiments, but the present invention is not intended to be limited to these Examples. Furthermore, in the following Examples and the like, the amount of incorporation is expressed in percent (%) by mass, unless particularly stated otherwise.

Emulsified cosmetic compositions having the compositions indicated in Table 1 and Table 2 described below were prepared, and the emulsified cosmetic compositions were evaluated on the following items by performing a test for actual usability by a panel of five experts. Furthermore, the stability of the various preparations was also evaluated. The results of the evaluations are presented together in Tables 1 and 2.

Evaluation items for the test for actual usability:
(1) Moistness
(2) Tautness

X: Evaluation point (average value) of equal to or more than 1.0 and less than 2.0

Evaluation of Preparation Stability:

The preparations of the various Examples were left to stand for 24 hours, and those preparations which did not undergo any change were rated as "○", while those preparations which underwent separation or gelation was rated as "X".

TABLE 1

|  | Example 1 | Example 2 | Example 3 | Example 4 | Example 5 | Comparative Example 1 |
|---|---|---|---|---|---|---|
| Purified water | Balance | Balance | Balance | Balance | Balance | Balance |
| Ethanol | 3 | 3 | 3 | 3 | 3 | 3 |
| Glycerin | 8 | 8 | 8 | 8 | 8 | 8 |
| Dipropylene glycol | 5 | 5 | 5 | 5 | 5 | 5 |
| Polyethylene glycol 20000 | 0.5 | 3 | 0.5 | 3 | 0.5 | 1 |
| Polyethylene glycol 1000 | — | — | — | — | — | — |
| Carboxyvinyl polymer | 0.1 | 0.1 | 0.1 | 0.1 | 0.1 | 0.15 |
| Acrylic acid-methacrylic acid alkyl copolymer | — | — | — | — | — | 0.05 |
| Xanthan gum | 0.1 | 0.1 | 0.1 | 0.1 | 0.1 | — |
| Polyvinyl alcohol | 0.05 | 0.05 | 0.1 | 0.1 | 1 | 0.05 |
| Potassium hydroxide | 0.1 | 0.1 | 0.1 | 0.1 | 0.1 | 0.001 |
| Isostearic acid | 0.5 | 0.5 | 0.5 | 0.5 | 0.5 | — |
| Stearic acid | 0.5 | 0.5 | 0.5 | 0.5 | 0.5 | — |
| Behenic acid | 0.5 | 0.5 | 0.5 | 0.5 | 0.5 | — |
| Polyoxyethylene (60) glyceryl isostearate | 1.0 | 1.0 | 1.0 | 1.0 | 1.0 | — |
| Polyoxyethylene (5) glyceryl monostearate | 1.0 | 1.0 | 1.0 | 1.0 | 1.0 | — |
| Behenyl alcohol | 0.5 | 0.5 | 0.5 | 0.5 | 0.5 | — |
| Liquid paraffin | 4 | 4 | 4 | 4 | 4 | — |
| Petrolatum | 1 | 1 | 1 | 1 | 1 | — |
| Cetyl 2-ethylhexanoate | 5 | 5 | 5 | 5 | 5 | 3 |
| Methylpolysiloxane | 2 | 2 | 2 | 2 | 2 | 1 |
| Tranexamic acid | 1 | 1 | 1 | 1 | 1 | 1 |
| Disodium edetate | 0.1 | 0.1 | 0.1 | 0.1 | 0.1 | 0.1 |
| Phenoxyethanol | 0.5 | 0.5 | 0.5 | 0.5 | 0.5 | 0.5 |
| Fragrance | q.s. | q.s. | q.s | q.s. | q.s. | q.s. |
| Moistness | ◎ | ◎ | ◎ | ◎ | ◎ | X |
| Tautness | ○ | ○ | ○ | ○ | ◎ | ○ |
| Stickiness | ○ | ◎ | ○ | ◎ | ○ | ○ |
| Softness of skin | ◎ | ◎ | ○ | ◎ | ○ | Δ |
| Preparation stability | ○ | ○ | ○ | ○ | ○ | ○ |

(3) Stickiness
(4) Softness of skin
Evaluation Method and Criteria:
Each of the evaluation items described above was subjected to a sensory evaluation and was scored by a five-grade score system based on the following evaluation criteria. Determinations were made on the basis of the following evaluation criteria, by using the average values of the scores.
(Score)
5 points: Excellent
4 points: Good
2 points: Poor
1 point: Very poor
(Evaluation Criteria)
◎: Evaluation point (average value) of equal to or more than 4.0 and equal to or less than 5.0
○: Evaluation point (average value) of equal to or more than 3.0 and less than 4.0
Δ: Evaluation point (average value) of equal to or more than 2.0 and less than 3.0

TABLE 2

|  | Comparative Examples | | | | | |
|---|---|---|---|---|---|---|
|  | 2 | 3 | 4 | 5 | 6 | 7 |
| Purified water | Balance | Balance | Balance | Balance | Balance | Balance |
| Ethanol | 3 | 3 | 3 | 3 | 3 | 3 |
| Glycerin | 8 | 8 | 8 | 8 | 8 | 8 |
| Dipropylene glycol | 5 | 5 | 5 | 5 | 5 | 5 |
| Polyethylene glycol 20000 | — | — | — | 8 | — | — |
| Polyethylene glycol 1000 | — | — | — | — | — | 3 |
| Carboxyvinyl polymer | 0.1 | 0.1 | 0.1 | 0.1 | 0.1 | 0.1 |
| Acrylic acid-methacrylic acid alkyl copolymer | — | — | — | — | — | — |
| Xanthan gum | 0.1 | 0.1 | 0.1 | 0.1 | 0.1 | 0.1 |
| Polyvinyl alcohol | — | 0.05 | 0.1 | 0.1 | 3 | 0.05 |
| Potassium hydroxide | 0.1 | 0.1 | 0.1 | 0.1 | 0.1 | 0.1 |

TABLE 2-continued

|  | Comparative Examples | | | | | |
| --- | --- | --- | --- | --- | --- | --- |
|  | 2 | 3 | 4 | 5 | 6 | 7 |
| Isostearic acid | 0.5 | 0.5 | 0.5 | 0.5 | 0.5 | 0.5 |
| Stearic acid | 0.5 | 0.5 | 0.5 | 0.5 | 0.5 | 0.5 |
| Behenic acid | 0.5 | 0.5 | 0.5 | 0.5 | 0.5 | 0.5 |
| Polyoxyethylene (60) glyceryl isostearate | 1.0 | 1.0 | 1.0 | 1.0 | 1.0 | 1.0 |
| Polyoxyethylene (5) glyceryl monostearate | 1.0 | 1.0 | 1.0 | 1.0 | 1.0 | 1.0 |
| Behenyl alcohol | 0.5 | 0.5 | 0.5 | 0.5 | 0.5 | 0.5 |
| Liquid paraffin | 4 | 4 | 4 | 4 | 4 | 4 |
| Petrolatum | 1 | 1 | 1 | 1 | 1 | 1 |
| Cetyl 2-ethylhexanoate | 5 | 5 | 5 | 5 | 5 | 5 |
| Methylpolysiloxane | 2 | 2 | 2 | 2 | 2 | 2 |
| Tranexamic acid | 1 | 1 | 1 | 1 | 1 | 1 |
| Disodium edetate | 0.1 | 0.1 | 0.1 | 0.1 | 0.1 | 0.1 |
| Phenoxyethanol | 0.5 | 0.5 | 0.5 | 0.5 | 0.5 | 0.5 |
| Fragrance | q.s. | q.s. | q.s. | q.s. | q.s. | q.s. |
| Moistness | ○ | ○ | ○ | ◎ | ○ | ○ |
| Tautness | X | ○ | ○ | ○ | ◎ | ○ |
| Stickiness | ○ | Δ | X | X | X | X |
| Softness of skin | ○ | ○ | Δ | ◎ | Δ | ○ |
| Preparation stability | ○ | ○ | ○ | ○ | X | ○ |

As is obvious from Table 2, Comparative Example 1 that was not emulsified with higher fatty acids, the moistness of the skin was poor, and Comparative Example 2 that did not contain polyvinyl alcohol could not give taut feeling. Furthermore, Comparative Examples 3 and 4 that did not contain any polyethylene glycol, and Comparative Example 5 that contained polyethylene glycol in an amount exceeding the predetermined range, caused stickiness. Further, Comparative Example 6 that did not contain any polyethylene glycol but contained polyvinyl alcohol in an amount exceeding the predetermined range, not only exhibited stickiness but also had poor stability of the preparation. In contrast to those preparations, Examples 1 to 5 according to the present invention had excellent taut feeling and were excellently free of stickiness. In the Examples, a satisfactory moist feeling and satisfactory softness were obtained, and the preparations were also stable. Furthermore, although a polyethylene glycol having an average molecular weight of less than 15000 was incorporated, stickiness could not be suppressed (Comparative Example 7).

Formulation Example 1

Milky Lotion

| Components | Contents (mass %) |
| --- | --- |
| Liquid paraffin | 7 |
| Petrolatum | 3 |
| Decamethylcyclopentasiloxane | 2 |
| Behenyl alcohol | 0.4 |
| Glycerin | 5 |
| Dipropylene glycol | 7 |
| Polyethylene glycol 1500 | 2 |
| Jojoba oil | 1 |
| Isostearic acid | 0.5 |
| Stearic acid | 0.5 |
| Behenic acid | 0.5 |
| Pentaerythrite tetra-2-ethylhexanoate | 3 |
| Cetyl 2-ethylhexanoate | 3 |
| Glyceryl monostearate | 1 |
| Polyoxyethylene glyceryl monostearate | 1 |
| 2-Amino-2-methyl-1,3-propanediol | 0.5 |
| Sodium hexametaphosphate | 0.05 |
| Stearyl glycyrrhetinate | 0.05 |
| 4-Methoxysalicylic acid potassium salt | 1 |
| L-arginine | 0.1 |
| Royal jelly extract | 0.1 |
| Yeast extract | 0.1 |
| Tocopherol acetate | 0.1 |
| Sodium acetylated hyaluronate | 0.1 |
| Trisodium edetate | 0.05 |
| Carboxyvinyl polymer | 0.15 |
| Paraben | q.s. |
| Purified water | Balance |
| Fragrance | q.s. |

Formulation Example 2

Cream

| Components | Contents (mass %) |
| --- | --- |
| Liquid paraffin | 3 |
| Petrolatum | 1 |
| Dimethylpolysiloxane | 1 |
| Stearyl alcohol | 1.8 |
| Behenyl alcohol | 1.6 |
| Glycerin | 8 |
| Dipropylene glycol | 5 |
| Macadamia nut oil | 2 |
| Hardened oil | 3 |
| Squalane | 6 |
| Stearic acid | 2 |
| Cholesteryl hydroxystearate | 0.5 |
| Cetyl 2-ethylhexanoate | 4 |
| Polyoxyethylene hardened castor oil | 0.5 |
| Self-emulsifying glyceryl monostearate | 3 |
| Triethanolamine | 0.8 |
| Sodiuum hexametaphosphate | 0.05 |
| Trimethylglycine | 2 |
| Retinol | 0.05 |
| Retinol acetate | 0.15 |
| Chinese blackberry extract | 0.1 |
| Phenoxyethanol | q.s. |
| Trisodium edetate | 0.05 |
| Coloring agent | q.s. |
| Carboxyvinyl polymer | 0.05 |
| Purified water | Balance |

Formulation Example 3

Protector

| components | Contents (mass %) |
| --- | --- |
| Petrolatum | 1 |
| Dimethylpolysiloxane | 3 |
| Methylphenylpolysiloxane | 3 |
| Stearyl alcohol | 0.5 |
| Glycerin | 7 |
| Dipropylene glycol | 3 |
| 1,3-Butylene glycol | 7 |
| Xylytol | 3 |
| Potassium α-tocopherol 2-L-ascorbate | 1 |

-continued

| components | Contents (mass %) |
|---|---|
| phosphate diester | |
| Tocopherol acetate | 0.1 |
| Squalane | 1 |
| Isostearic acid | 0.5 |
| Stearic acid | 0.5 |
| Polyoxyethylene glyceryl monostearate | 1 |
| Glyceryl monostearate | 2 |
| Potassium hydroxide | 0.05 |
| L-ascorbyl magnesium phosphate | 0.1 |
| Sodium acetylated hyaluronate | 0.1 |
| Trisodium EDTA | 0.05 |
| 4-t-butyl-4'-methoxydibenzoylmethane | 2 |
| 2-Ethylhexyl paramethoxycinnamate | 5 |
| Carboxyvinyl polymer | 0.1 |
| Phenoxyethanol | q.s. |
| Purified water | Balance |
| Fragrance | q.s. |

Formulation Example 4

Sunblock Cream

| Components | Contents (mass %) |
|---|---|
| Methylphenylpolysiloxane | 5 |
| Stearyl alcohol | 2 |
| Glycerin | 5 |
| Dipropylene glycol | 5 |
| Sorbite solution (70%) | 5 |
| Stearic acid | 1.5 |
| Palmitic acid | 1 |
| Pentaerythrite tetra-2-ethylhexanoate | 4 |
| Self-emulsifying glyceryl monostearate | 1 |
| 2-Amino-2-methyl-1-propanol | 0.3 |
| Octyl methoxycinnamate | 6 |
| Petrolatum | 2 |
| Tranexamic acid | 2 |
| Dipotassium glycyrrhizinate | 0.05 |
| Pantothenyl ethyl ether | 0.05 |
| 1,3-Butylene glycol | 4 |
| Squalane | 3 |
| Sodium citrate | 0.1 |
| Sodium acetylated hyaluronate | 0.1 |
| Xanthan gum | 0.2 |
| Bentonite | 1 |

-continued

| Components | Contents (mass %) |
|---|---|
| Paraben | q.s. |
| Purified water | Balance |
| Fragrance | q.s. |

It will be further understood that the proposed invention also includes a method for preparing an emulsified cosmetic composition wherein the steps for such preparation include the combination of the elements as noted herein.

It will be further understood that terms, such as those defined in commonly used dictionaries, should be interpreted as having a meaning that is consistent with their meaning in the context of the specific scientific relevant art and will not be interpreted in an idealized or overly formal sense unless expressly so defined herein. In the specification, there have been disclosed typical embodiments of the invention and, although specific terms are employed, they are used in a descriptive sense and not for purposes of limitation, the scope of the invention being set forth in the following claims.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

The invention claimed is:

1. An emulsified cosmetic composition comprising:
   (a) 0.01% to 1% by mass polyvinyl alcohol;
   (b) 0.01% to 5% by mass a polyethylene glycol having a molecular weight of 15,000 to 25,000; and
   an emulsifying amount of a soap formed from a higher fatty acid and a neutralizing agent.

2. The cosmetic composition according to claim 1, wherein: the higher fatty acid is at least one fatty acid having 14 to 22 carbon atoms.

3. The cosmetic composition according to claim 1, wherein: the higher fatty acid is a mixture of behenic acid, isostearic acid and stearic acid.

4. The cosmetic composition according to claim 1, further comprising: a nonionic surfactant.

5. The cosmetic composition according to claim 2, further comprising: a nonionic surfactant.

6. The cosmetic composition according to claim 3, further comprising: a nonionic surfactant.

* * * * *